US006339100B1

(12) United States Patent
Longley

(10) Patent No.: US 6,339,100 B1
(45) Date of Patent: Jan. 15, 2002

(54) METHODS FOR INHIBITING MASTOCYTOSIS

(75) Inventor: B. Jack Longley, Hamden, CT (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/474,474

(22) Filed: Dec. 29, 1999

(51) Int. Cl.$^7$ .................. A61K 31/40; A61K 31/495
(52) U.S. Cl. .......................... 514/412; 514/255
(58) Field of Search ................. 514/412, 255

(56) References Cited

U.S. PATENT DOCUMENTS

| | | | |
|---|---|---|---|
| 5,883,116 A | 3/1999 | Tang et al. | 514/418 |
| 5,905,149 A | 5/1999 | Battistini et al. | 544/128 |

FOREIGN PATENT DOCUMENTS

| | | |
|---|---|---|
| WO | WO9910325 | 3/1999 |
| WO | WO9961422 | 12/1999 |

OTHER PUBLICATIONS

Anderson, D.M., et al. (1990) "Molecular cloning of mast cell growth factor, a hematopoietin that is active in both membrane bound and soluble forms" Cell, 63:235–243 (Exhibit 1).

Bradl, M., et al. (1991) "Clonal coat color variation due to a transforming gene expressed in melanocytes of transgenic mice" Proc. Nat. Acad. Sci. USA 88:6447–6451; (Exhibit 2).

Costa, J. J. et al. (1996) "Recombinant human stem cell factor (KIT ligand) promotes human mast cell and melanocyte hyperplasia and functional activation in vivo" J. Exp. Med 183: 2681–2686; (Exhibit 3).

Funasaka, Y., et al. (1992) "C–kit–kinasse induces a cascade of protein tyrosine phosphorylation in normal human melanocytes in respnse to mast cell growth factor and stimulates mitogen–activated protein kinase but is down–regulated in melanomas" Mol. Biol. Cell, 3:197–209; (Exhibit 4).

Furitsu, T., et al. (1993) Identification of mutations in the coding sequence of the proto–oncogene c–kit in human mast cell leuemia cell line causing ligand independent activation of c–KIT product J. Clin. Invest., 92:1736–1744; (Exhibit 5).

Grichnik, J. M., et al. (1995) "Human recombinant stemcell factor induces melanocytic hyperplasia in susceptible patients" J. Am. Acad. Dermol., 33: 577–583; (Exhibit 6).

Hamann, K., et al. (1995) "Expression of stem cell factor in cutaneous mastocytosis" Br. J. Dermatol., 133: 203–208; (Exhibit 7).

Harrist, T.J., et al. (1995) Recombinant human stem cell factor in (SCF) (c–kit ligand promotes melanocytes hyperplasia and activation in vivo Lab. Invest., 72:48A; (Exhibit 8).

Hirobe, T. (1984) "Histochemical survey of the distribution of the epidermal melanoblasts and melanocytes in the mouse during fetal and postnatal periods" Anat. Rec., 208:589–594; (Exhibit 9).

Longley, B. J. et al. (1993) "Altered metabolism of mast–cell growth factor (c–kit ligand) in cutaneous mastocytosis" N. Engl. J. Med. . 328:1302–1307; (Exhibit 10).

Longley, B. J. et al. (1995) "The mast cell and mast cell disease" J. Am. Acad. Dermatol., 32:545–561; (Exhibit 11).

Longley, B. J., et al. (1996) "Somastic c–KIT activating mutation in urticaria pigmentosa and aggressive mastocytosis: establishment of clonality in a human mast cell neoplasm" Nature Genetics, 12:312–314; (Exhibit 12).

Lu, H. S., et al. (1991) "Amino acid sequence and post–translational modification of stem cell factor isolated from buffalo rat liver cell–conditioned medium" J. Biol. Chem., 266:8102–8107; (Exhibit 13).

Nishikawa, S., et al. (1991) "In utero manipulation of coat color formation by a monoclonal anti–c–kit antibody: two distinct waves of c–kit–dependency during melanocyte development" EMBO J. 10:2111–2118; (Exhibit 14).

Okura, M., et al. (1995) "Effects of monoclonal anti–c–kit antibody (AKC2) on melanocytes in newborn mice" J. Invest. Dermatol., 105:322–328; (Exhibit 15).

Tsai, M., et al. (1991) "The rat c–kit ligand, stem cell factor, induces the development of connective tissue–type and mucosal mast cells in vivo: analysis by anatomical distribution, hisochemistry, and protease phenotype" J. Exp. Med., 174:125–131; (Exhibit 16).

Vassar, R., et al. (1989) "Tissue–specific and differentiation–specific expression of a human K14 keratin gene in transgenic mice" Proc. Natl. Acad. Sci. USA, 86:1563–1567; (Exhibit 17).

Weiss, R. R. et al. (1995) "Human dermal endothelial cells express membrane–associated mast cell growth factor" J. Invest. Dermatol. 104:101–106; (Exhibit 18).

(List continued on next page.)

Primary Examiner—Theodore J. Criares
Assistant Examiner—Jennifer Kim
(74) Attorney, Agent, or Firm—John P. White; Cooper & Dunham LLP

(57) ABSTRACT

A method of preventing or treating in a subject mastocytosis which comprises administering to the subject a therapeutically effective amount of a compound having the structure:

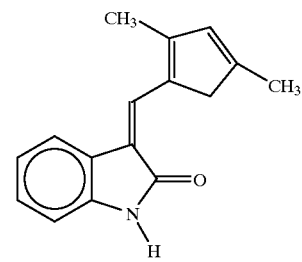

or a pharmaceutically acceptable salt thereof so as to thereby prevent or treat mastocytosis in the subject.

20 Claims, 2 Drawing Sheets

OTHER PUBLICATIONS

Williams, D.E., et al. (1990) "Identification of a ligand for the c–kit proto–oncogene" Cell, 1990; 63:167–174; (Exhibit 19).

Yarden, Y., et al. (1987) "Human proto–oncogene c–kit: a new cell surface receptor tyrosine kinase for an unidentified ligand" EMBO J. 6:3341–3351; (Exhibit 20).

Yoshida, H., et al. (1996) "Distinct stages of melanocyte differentiation revealed by analysis of nonuniform pigmentation patterns" Development, 122:1207–1214; (Exhibit 21).

Yohida, H. et al. (1996) "Neural and skin cell– specific expression pattern conferred by Steel factor regulatory sequence in transgenic mice" Development Dynamic, 207:222–232; (Exhibit 22).

Zsebo, K. M., et al. (1990) "Stem cell factor is encoded at the S1 locus of the mouse and is the ligand for the c–kit tyrosine kinase receptor" Cell, 63:213–224; (Exhibit 23).

Devinney R, Gold WV: Establishment of two dog mastocytoma cell lines in continuous culture. *Am J Respir Cell Mol Biol* 3: 413–420, 1990 (Exhibit 24).

Dunn TB, Potter M: A transplantable mast–cell neoplasm in the mouse. *J Natl Cancer Inst* 18: 587–601, 1957 (Exhibit 25).

Lazarus SC, DeVinney R, McCabe LJ, Finkbeiner WE, Elias DJ, Gold WM: Isolated canine , 1986 mastocytoma cells: propagation and characterization of two cell lines. *Am J Physiol* 251: C935–944 (Exhibit 26).

Martin FH, Suggs SV, Langley KE, Lu HS, Ting J, et al: Primary structure and functional expression of rat and human stem cell factor DNAs. *Cell* 63: 203–211, 1990 (Exhibit 27).

Mohammadi M, McMahon G, Sun L, Tang C, Hirth P, et al: Structures of the tyrosine kinase domain of fibroblast growth factor receptor in complex with inhibitors. *Science* 276: 955–960, 1997 (Exhibit 28).

Piao X, Paulson R, Van Der Geer P, Pawson T, Berstein A: Oncogenic mutation in the Kit receptor tyrosine kinase alters substrate specificity and induces degradation of the protein tyrosine phosphatase SHP–1. *Proc Natl Acad Sci USA* 93: 14665–14669, 1996 (Exhibit 29).

Qiu F, Ray P, Brown K, Barker PE, Jhanwar S, et al: Primary structure of c–kit: relationship with the CSF–1/PDGF receptor kinase family–oncogenic activation of v–kit involves deletion of extracellular domain and C terminus. *EMBO J* 7: 1003–1011, 1988 (Exhibit 30).

Sun L, Tran N, Tang F, App H, Hirth P, McMahon G, Tang C: Synthesis and biological evaluations of 3–substituted indolin–2–ones: a novel class of tyrosine kinase inhibitors that exhibit selectivity toward particular receptor tyrosine kinases. *J Med Chem* 41: 2588–2603, 1998 (Exhibit 31).

Tsujimura T, Furitsu T, Morimoto M, Koji K, Nomura S, et al: Ligand–independent activation of c–kit receptor tyrosine kinase in a murine mastocytoma cell line P–815 generated by a point mutation. *Blood* 83: 2619–2626, 1994 (Exhibit 32).

Schrader, John W. and Thomas, Wayne R. "Delayed Hypersensitivity in Mast–Cell–Deficient Mice", *The Journal of Immunology*. (1983), vol. 130, No. 6, pp. 2565–2567 (Exhibit 33).

Galli, Stephen J. and Mekori, Yoseph A., "Undiminished Immunologic Tolerance to Contact Sensitivity in Mast Cell-Deficient W/Wv and S1/S1d Mice1", *The Journal of Immunology*. (1995), vol. 135, No. 2, pp. 879–885 (Exhibit 34).

Askenase, Philip W., Loveren, Henk Van, Kraeuter–Kops, Sandra, Ron, Yacov, Meade, Robin, Theoharides, Theoharis C., Nordlund, James J., Scovern, Henry, Gerhson, Michael D., and Ptak, Wlodzimierz., "Defective Elicitation of Delayed–Type Hypersensitivity in W/Wv and SI/SId Mast Cell–Deficient Mice1", *The Journal of Immunology*. (1983), vol. 131, No. 6, pp. 2687–2693 (Exhibit 35).

METHODS FOR INHIBITING MASTOCYTOSIS

The invention described herein was made with Government support under grant numbers RO1 AR43356 and P30 AR44535 from the National Institutes of Health. Accordingly, the United States Government has certain rights in this invention.

Throughout this application, various publications are referenced within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

Mastocytosis is a neoplastic disease caused at least in part by somatic mutations of the c-KIT proto-oncogene resulting in constitutive activation of its protein product, KIT, the receptor tyrosine kinase for stem cell factor. KIT stimulates mast cell proliferation and prevents apoptosis of neoplastic mast cells. To develop potential therapies for mastocytosis we used indolinones, small molecules which inhibit tyrosine kinases. An indolinone derivative with structure VI (see below) or structure VII inhibited wild-type KIT, but variably inhibited constitutively activated KIT mutants. The compounds with structure VI or structure VII were effective against KIT with juxtamembrane activating mutations. Furthermore, the compounds with structure VI or structure VII killed neoplastic mast cells expressing a juxtamembrane-mutated KIT, whereas the compound with structure VII killed neoplastic mast cells expressing KIT bearing a kinase domain mutation. These data show a direct correlation between inhibition of constitutively activated KIT and the death of neoplastic mast cells, and point to specific tyrosine kinase inhibitors as a novel therapy aimed directly at a cause of mastocytosis.

SUMMARY OF THE INVENTION

This invention provides a method of preventing or treating in a subject mastocytosis which comprises administering to the subject a therapeutically effective amount of a compound having the structure:

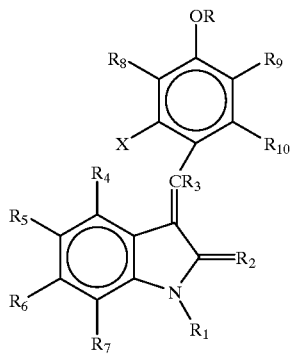

(Structure I)

or a pharmaceutically acceptable salt thereof so as to thereby prevent or treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

$R_8$, $R_9$, and $R_{10}$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

n is 0–3; x is Br, Cl, F or I; each of R and R' is independently H, alkyl or aryl.

This invention provides a method of preventing or treating in a subject mastocytosis which comprises administering to the subject a therapeutically effective amount of a compound having the structure:

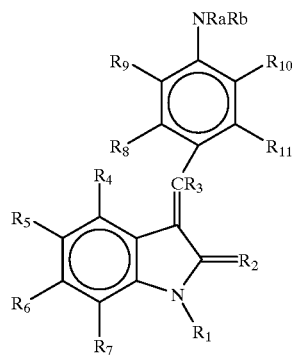

(Structure II)

or a pharmaceutically acceptable salt thereof so as to thereby prevent or treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

$R_8$, $R_9$, $R_{10}$ and $R_{11}$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

Ra and Rb are each independently hydrogen, alkyl and C(O)R, or NRaRb taken together may be a heterocyclic ring of 3 to 8 atoms optionally substituted at one or more positions with hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

n is 0–3; x is Br, Cl, F or I; and each of R and R' is independently H, alkyl or aryl.

This invention provides a method of preventing or treating in a subject mastocytosis which comprises administering to the subject a therapeutically effective amount of a compound having the structure:

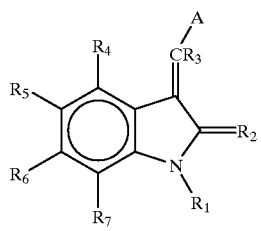

(Structure III)

or a pharmaceutically acceptable salt thereof so as to thereby prevent or treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

A is a five membered heteroaryl ring thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, or tetrazole, optionally substituted at one or more positions with alkyl, alkoxy, aryl, aryloxy, alkaryl, alkaryloxy, halogen, trihalomethyl, S(O)R, $SO_2NRR'$, $SO_3R$, SR, NO2, NRR', OH, CN, C(O)R, OC(O)R, NHC(O)R, $(CH_2)_nCO2R$, or CONRR';

n is 0–3; x is Br, Cl, F or I; and each of R and R' is independently H, alkyl or aryl.

This invention provides a method of preventing or treating in a subject mastocytosis which comprises administering to the subject a therapeutically effective amount of a compound having the structure:

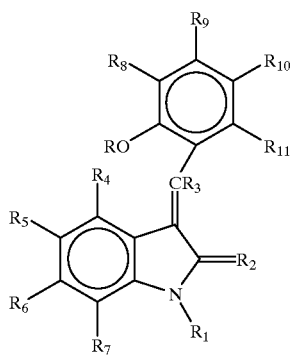

(Structure IV)

or a pharmaceutically acceptable salt thereof so as to thereby prevent or treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

$R_8$, $R_9$ and $R_{10}$ and $R_{11}$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

n is 0–3; x is Br, Cl, F or I; each of R and R' is independetly H, alkyl or aryl.

This invention provides a method of preventing or treating in a subject mastocytosis which comprises administering to the subject a therapeutically effective amount of a compound having the structure:

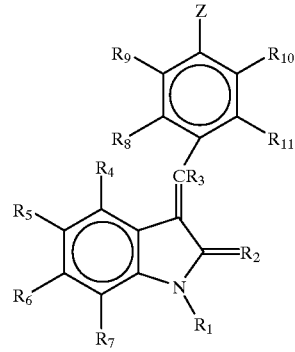

(Structure V)

or a pharmaceutically acceptable salt thereof so as to thereby prevent or treat mastocytosis in the subject, wherein RI is HI or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR ', OH, CN, C(O)R, OC(O)R, NHC(O)R, $(CH_2)_nCO2R$, or CONRR';

$R_8$, $R_9$, $R_{10}$ and $R_{11}$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

n is 0–3; Z is Br, Cl, F, I, methyl, ethyl, n-propyl, iso-propyl, n-butyl, iso-butyl, or tert-butyl; and each of R and R' is independently H, alkyl or aryl.

This invention provides a method of preventing or treating in a subject mastocytosis which comprises administering to the subject a therapeutically effective amount of a compound having the structure:

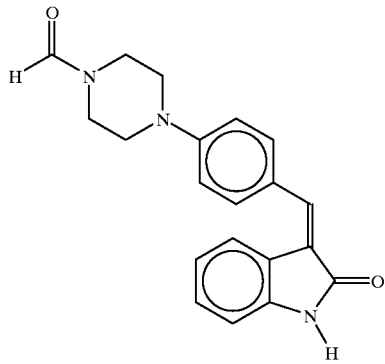

(Structure VI)

or a pharmaceutically acceptable salt thereof so as to thereby prevent or treat mastocytosis in the subject.

This invention provides a method of preventing or treating in a subject mastocytosis which comprises administering to the subject a therapeutically effective amount of a compound having the structure:

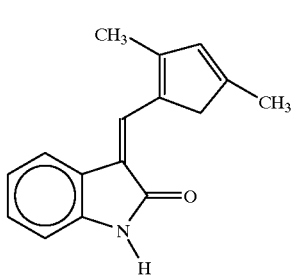

(Structure VII)

or a pharmaceutically acceptable salt thereof so as to thereby prevent or treat mastocytosis in the subject.

This invention provides a method of preventing or treating in a subject mastocytosis which comprises administering to the subject a therapeutically effective amount of a compound having the structure:

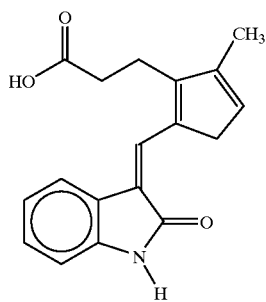

(Structure VIII)

or a pharmaceutically acceptable salt thereof so as to thereby prevent or treat mastocytosis in the subject.

DETAILED DESCRIPTION OF THE INVENTION

Figure 1:
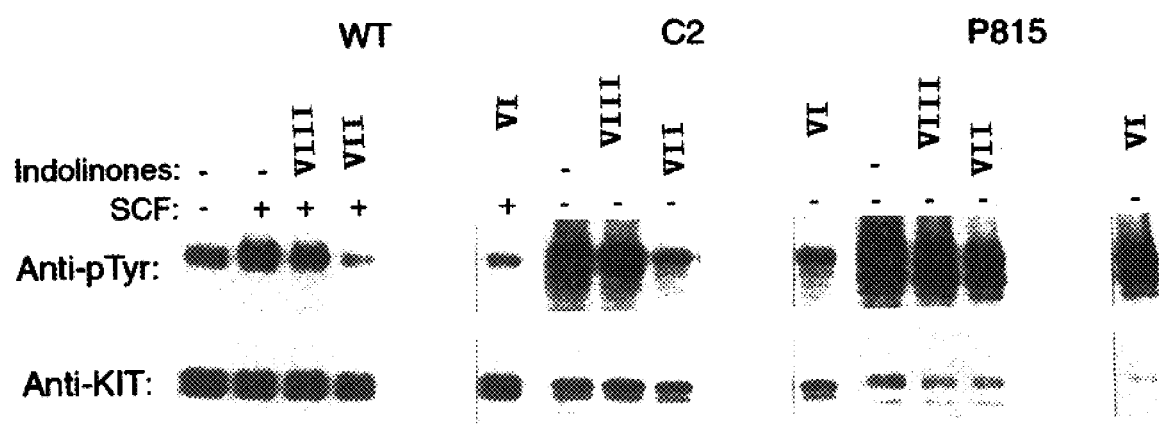
FIG. 1: Effects of indolinone derivatives on phosphorylation of wild-type and mutant KITs. (a) Anti-phosphotyrosine (pTyr) blots of immunoprecipitated wild-type (WT) KIT expressed in COS cells and of mutant KITs expressed in C2 and P815 cells stimulated (+), or not (−), with stem cell factor (SCF, 100 ng/ml, 10 min) after incubation (+), or not (−), with indolinone derivatives (5 μM for COS and C2 cells, 40 μM for P815 cells, 30 min) show that the compound with structure VII or structure VI inhibit wild-type KIT phosphorylation but variably inhibit C2 and P815 KIT phosphorylation. The compound with the structure VII or structure VI are effective against KIT containing an activating juxtamembrane domain mutation in C2 cells. (b) Re-probing the anti-pTyr blots (after stripping) with anti-KIT antibody shows that comparable amounts of receptor are present in different lanes.

This invention provides a method of preventing or treating in a subject mastocytosis which comprises administering to the subject a therapeutically effective amount of a compound having the structure:

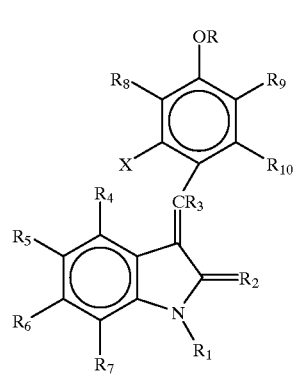

(Structure I)

or a pharmaceutically acceptable salt thereof so as to thereby prevent or treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

$R_8$, $R_9$, and $R_{10}$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

n is 0–3; x is Br, Cl, F or I; each of R and R' is independently H, alkyl or aryl.

This invention provides a method of preventing or treating in a subject mastocytosis which comprises administering to the subject a therapeutically effective amount of a compound having the structure:

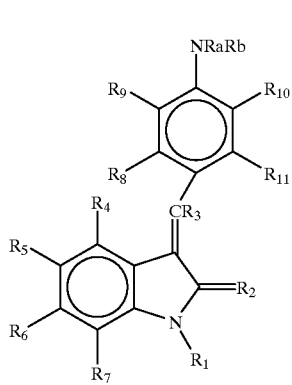

(Structure II)

or a pharmaceutically acceptable salt thereof so as to thereby prevent or treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO2R$, or CONRR';

$R_8$, R, $R_{10}$ and $R_{11}$ are each independently hydrogen, alkyl, alkoxy, aryl, aryloxy, alkaryl, alkaryloxy, halogen, trihalomethyl, S(O)R, $SO_2NRR'$, $SO_3R$, SR, NO$_2$, NRR', OH, CN, C(O)R, OC(O)R, NHC(O)R, (CH$_2$)$_n$CO2R, or CONRR';

Ra and Rb are each independently hydrogen, alkyl and C(O)R, or NRaRb taken together may be a heterocyclic ring of 3 to 8 atoms optionally substituted at one or more positions with hydrogen, alkyl, alkoxy, aryl, aryloxy, alkaryl, alkaryloxy, halogen, trihalomethyl, S(O)R. SO$_2$NRR', SO$_3$R, SR, NO$_2$, NRR', OH, CN, C(O)R, OC(O)R. NHC(O)R, (CH$_2$)$_n$CO2R, or CONRR';

n is 0–3; x is Br, Cl, F or I; and each of R and R' is independently H, alkyl or aryl.

This invention provides a method of preventing or treating in a subject mastocytosis which comprises administering to the subject a therapeutically effective amount of a compound having the structure:

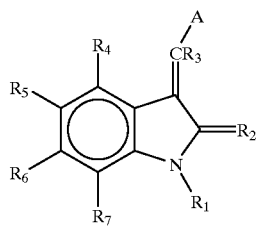

(Structure III)

or a pharmaceutically acceptable salt thereof so as to thereby prevent or treat mastocytosis in the subject, wherein R$_1$ is H or alkyl; R$_2$ is O or S; R$_3$ is hydrogen;

R$_4$, R$_5$, R$_6$, and R$_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

A is a five membered heteroaryl ring thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, or tetrazole, optionally substituted at one or more positions with alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; x is Br, Cl, F or I; and each of R and R' is independently H, alkyl or aryl.

This invention provides a method of preventing or treating in a subject mastocytosis which comprises administering to the subject a therapeutically effective amount of a compound having the structure:

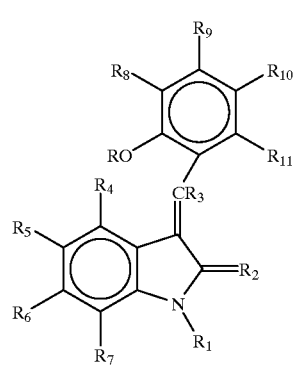

(Structure IV)

or a pharmaceutically acceptable salt thereof so as to thereby prevent or treat mastocytosis in the subject, wherein R$_1$ is H or alkyl; R$_2$ is O or S; R$_3$ is hydrogen;

R$_4$, R$_5$, R$_6$, and R$_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$) CO2R, or CONRR';

R$_8$, R$_9$ and R$_{10}$ and R$_{11}$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; x is Br, Cl, F or I; each of R and R' is independently H, alkyl or aryl.

This invention provides a method of preventing or treating in a subject mastocytosis which comprises administering to the subject a therapeutically effective amount of a compound having the structure:

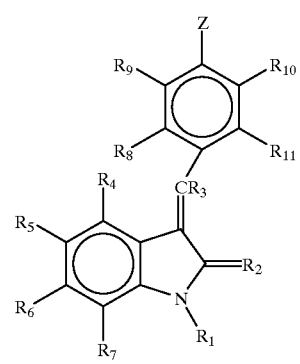

(Structure V)

or a pharmaceutically acceptable salt thereof so as to thereby prevent or treat mastocytosis in the subject, wherein R$_1$ is H or alkyl; R$_2$ is O or S; R3 is hydrogen;

R$_4$, R$_5$, R$_6$, and R$_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

R$_8$, R$_9$, R$_{10}$ and R$_{11}$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; Z is Br, Cl, F, I, methyl, ethyl, n-propyl, iso-propyl, n-butyl, iso-butyl, or tert-butyl; and each of R and R' is independently H, alkyl or aryl.

This invention provides a method of preventing or treating in a subject mastocytosis which comprises administering to the subject a therapeutically effective amount of a compound having the structure:

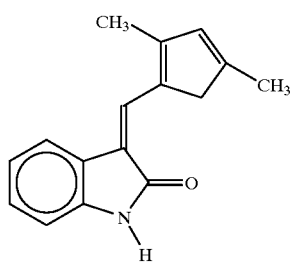

(Structure VI)

or a pharmaceutically acceptable salt thereof so as to thereby prevent or treat mastocytosis in the subject.

This invention provides a method of preventing or treating in a subject mastocytosis which comprises administering to the subject a therapeutically effective amount of a compound having the structure:

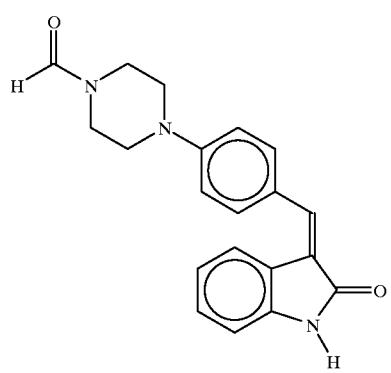

(Structure VII)

or a pharmaceutically acceptable salt thereof so as to thereby prevent or treat mastocytosis in the subject.

This invention provides a method of preventing or treating in a subject mastocytosis which comprises administering to the subject a therapeutically effective amount of a compound having the structure:

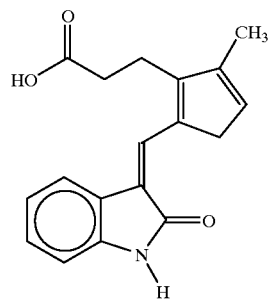

(Structure VIII)

or a pharmaceutically acceptable salt thereof so as to thereby prevent or treat mastocytosis in the subject.

In one embodiment, the above method comprises inhibiting the kinase enzymatic reaction of kit protein. In one embodiment, the method comprises inhibiting chymase, elastase or other SCF cleaving enzymes. In one embodiment, the method comprises inhibiting ligand binding with an antibody, peptide, or nonpeptide chemical. In one embodiment, the method comprises inhibiting kit dimerization with an antibody, peptide, or nonpeptide chemical. In one embodiment of the above method, downstream signaling of the kit activation pathway is inhibited by blocking substrate association with kit kinase domain. In another embodiment of the above method, downstream signaling of the kit activation pathway is inhibited by blocking enzymatic function in the downstream signaling pathway. In another embodiment of the above method, the downstream signaling of the kit activation pathway is inhibited by blocking binding of molecules in the downstream signaling pathway.

The subject of the above methods includes but is not limited to a mammal. The subject may be a mammal or non-mammal. The subject may be a human, a primate, an equine subject, an opine subject, an avian subject, a bovine subject, a porcine, a canine, a feline or a murine subject. In another embodiment, the subject is a vertebrate. In a preferred embodiment, the mammal is a human being.

In another embodiment of the above methods, the compound is a small molecule or peptide. In one embodiment, the compound has the following structure or a pharmaceutically acceptable salt thereof:

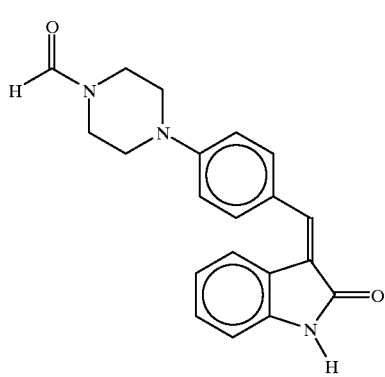

(Structure VII)

In one embodiment, the compound has the following structure or is a pharmaceutically acceptable salt thereof:

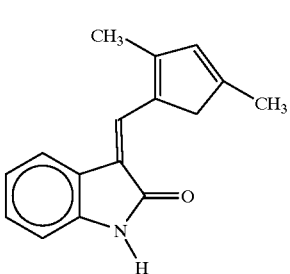

(Structure VI)

The subject of this method includes but is not limited to a canine or a human being.

In one embodiment of the above methods, the compound is admixed with a carrier.

In one embodiment of the above methods, the administration is intralesional, intraperitoneal, intramuscular, subcutaneous, intravenous, liposome mediated delivery, transmucosal, intestinal, topical, nasal, oral, anal, ocular or otic delivery.

In one embodiment of the above methods, the therapeutically effective amount is from about 1 mg/kg to about 1000 mg/kg. In one embodiment of the above methods, the therapeutically effective amount is from about 50 mg/kg to about 200 mg/kg.

In one embodiment of the above methods, the pharmaceutically acceptable salt is a hydrochloride salt, a mesylate salt, an ethylsulfonate salt, or a sulfate salt.

This invention will be better understood from the Experimental Details which follow. However, one skilled in the art will readily appreciate that the specific methods and results discussed are merely illustrative of the invention as described more fully in the claims which follow thereafter.

Experimental Details

The proto-oncogene c-KIT encodes KIT (Yarden et al, 1987; Qiu et al, 1988), the receptor tyrosine kinase for stem cell factor (Martin et al, 1990), also known as mast cell growth factor. Somatic c-KIT mutations causing ligand-independent activation of KIT and cell transformation (Furitsu et al, 1993; Kitayama et al, 1995; Tsujimura et al, 1996; Hirota et al, 1998; Ma et al, 1999a) appear causal in certain types of mastocytosis (Nagata et al, 1995; Longley et al, 1996, 1999; Ma et al, 1999a).

Documented activating c-KIT mutations fall into two groups. One group consists of mutations in codon 816 of human c-KIT, or its equivalent positions in other species, resulting in single residue substitution for Asp816 in the activation loop of the receptor kinase domain (Ma et al, 1999a). The other group of activating mutations includes single residue substitutions and in-frame insertions or deletions in the receptor intracellular juxtamembrane region, which disrupt intramolecular inhibition of the kinase by a putative juxtamembrane α-helix (Ma et al, 1999b). All sporadic adult-onset mastocytosis patients examined to date, and a subset of pediatric cases with atypical clinical presentations, have activating codon 816 mutations (Longley et al, 1999), whereas activating juxtamembrane mutations are common in canine mastocytomas (Ma et al, 1999a) and in human gastrointestinal stromal tumors (Hirota et al, 1998).

It is shown that inhibition of KIT by indolinone derivatives is sufficient to kill neoplastic mast cells. These results support a causal role for activating c-KIT mutations in the pathogenesis of mastocytosis and identify tyrosine kinase inhibitors as a novel therapy targeting a cause of mastocytosis.

Materials and Methods

Compounds Indolinones are polycyclic compounds which bind the ATP binding pocket of receptor tyrosine kinases, inhibiting their activities (Mohammadi et al, 1997; Sun et al, 1998). Several indolinone derivatives were used in the present study:

(a) the compound with following structure:

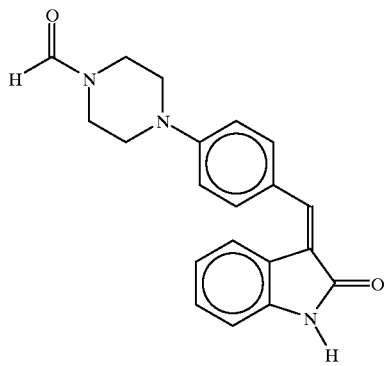

(Structure VII)

(b) the compound with the following structure:

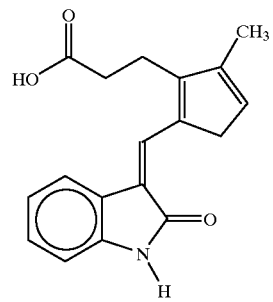

(Structure VIII)

(c) the compound with the following structure:

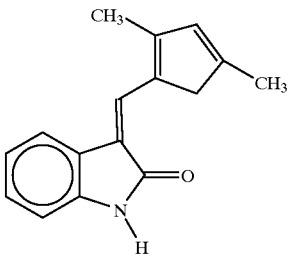

(Structure VI)

The compound with structure VII has a relatively broad spectrum of inhibition, being effective against platelet-derived growth factor receptor, fibroblast growth factor receptor, and insulin receptor, while the compound with structure VIII effectively inhibits the fibroblast growth factor receptor (Mohammadi et al, 1997; Sun et al, 1998). The compound with structure VI suppresses vascular endothelial growth factor receptor and the platelet-derived growth factor receptor. (Sun L, Tran N, Tang F, Schreck R, Fong TAT, McMahon G, Tang C: Synthesis and biological evaluation of novel 3-(substituted pyrrol-2-yl)indolin-2-ones as potent and selective inhibitors of the Flk-1/KDR receptor tyrosine kinase. 215th ACS National Meeting, Dallas, MEDI-169, 1998 (Abstr.); Sun L, Tran N, Liang C, Tang F, Rice A, Schreck R, Waltz K, Shawver L, McMahon G, Tang C: Design, synthesis, and evaluations of substituted 3-[(3- or 4-carboxyethylpyrrol-2-yl)methylindenyl]indolin-2-ones as inhibitors of VEGF, PDGF, and FGF receptor tyrosine kinases. The potential activities of these compounds on KIT have not been previously reported.

Assays

KIT activity was determined by in vitro phosphorylation, as previously described (Ma et al, 1999a). The neoplastic mast cell line C2 and P815 have been previously described (Dunn et al, 1957; Lazarus et al, 1986; DeVinney and Gold, 1990), and their activating c-KIT mutations characterized (Tsujimura et al, 1994; Ma et al, 1999a). To determine cell proliferation and viability, cells from triplicate cultures were stained with trypan blue and counted in a hemocytometer. All experiments were repeated at least three times.

Results and Discussion

The effects of indolinone derivatives on the activity of wild-type KIT were first examined. A compound with structure VII or structure VI could substantially reduce tyrosine phosphorylation of the wild-type receptor at 5 $\mu$M concentration, while the compound of structure VIII could only slightly decrease the receptor phosphorylation at this concentration (FIG. 1).

The effects of these compounds on constitutive activation of KIT mutants expressed by neoplastic mast cells were then tested. For activating juxtamembrane mutations, the C2 dog mastocytoma cell line was studied (Lazarus et al, 1986; DeVinney and Gold, 1990), in which KIT is constitutively active due to a juxtamembrane insertion mutation (Ma et al, 1999a). Treatment of the cells with 5 $\mu$M of the compound with structure VII or structure VI resulted in approximately 50% reduction of the constitutive C2 KIT phosphorylation (FIG. 1). In contrast, 5 $\mu$M of the compound of structure VIII could barely repress the receptor phosphorylation. The effects of these compounds on constitutive phosphorylation of KIT bearing in the juxtamembrane region either deletion of Trp556-Lys557 or substitution of Pro for Leu575, mutations previously identified in dog mastocytomas (Ma et al, 1999a) were also examined. Similar inhibitory effects were observed with the additional mutant receptors (data not shown).

For activating mutations in the kinase domain, the P815 murine mast cell tumor line (Dunn et al, 1957) was examined. P815 c-KIT contains a point mutation resulting in substitution of Tyr for Asp814, the equivalent position of human Asp816, which causes constitutive receptor activation (Tsujimura et al, 1994).

To determine whether these compounds might be useful therapeutically for mast cell tumors, the effects on C2 and P815 cell proliferation was examined. As shown in FIG. 11, C2 cells were killed by treating them daily with 1 $\mu$M of the compound of structure VII or structure VI. By comparison, the compound of structure VIII only retarded the C2 cell proliferation at this concentration. These results were consistent with the effects of the five compounds on the phosphorylation of KIT expressed by C2 cells (FIG. 1).

Figure 2:
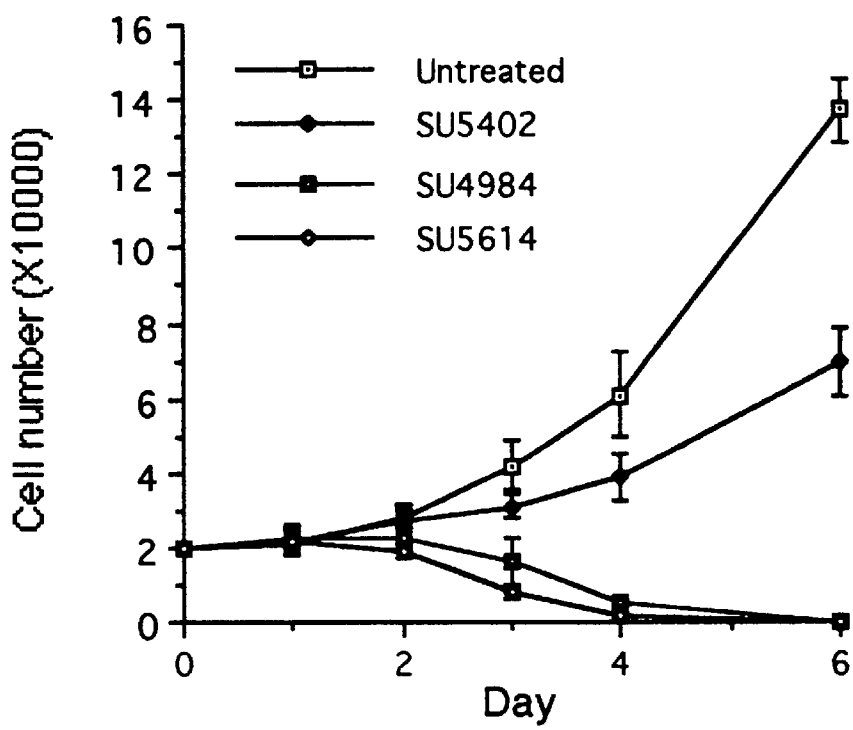
FIG. 2: Effects of indolinone derivatives on neoplastic mast cell growth. Cell proliferation assay of C2 and P815 cells treated daily with 1 μM and 10 μM, respectively, of indolinone derivatives shows that the compound with structure VII or structure VI kill C2 cells, and the compound with structure VII kill P815 cells. Results (mean±SEM) represent averages of triplicate cultures.
Figure 2:
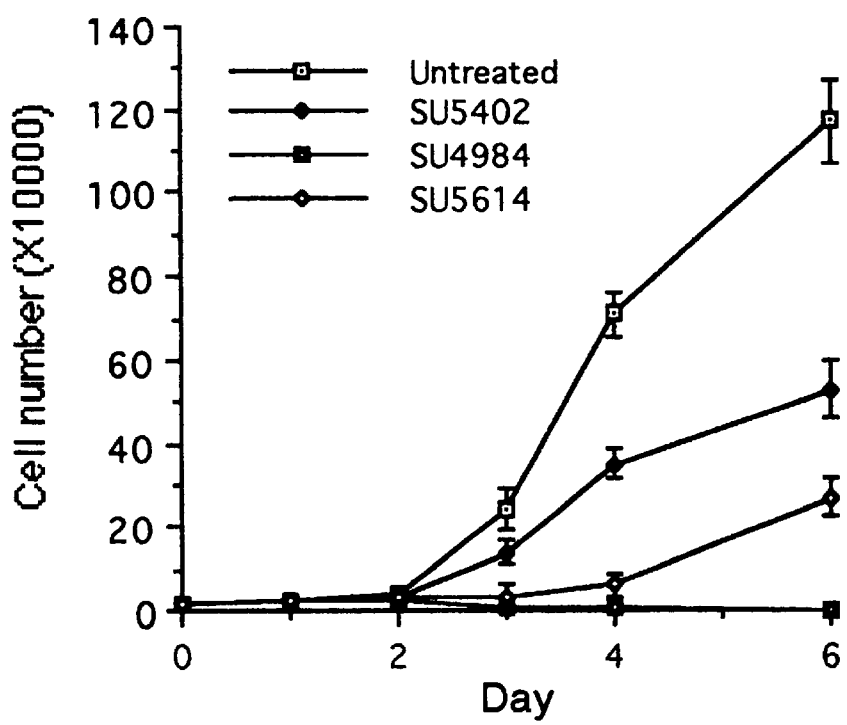

The proliferation of P815 cells was not affected by treating the cells daily with the compounds at 1 $\mu$M concentration. However, the compound with structure VII killed the P815 cells at 10 $\mu$M concentration, whereas the compound with structure VIII or structure VI showed only inhibition of the cell proliferation at this concentration (FIG. 2). The requirement of an order of magnitude or more of the compound of structure VII to kill P815 cells in comparison with their effects on C2 cells might be related to the difference in the in vivo behavior of these two cell lines. P815 cells are able to rapidly form metastasizing tumors in syngenic mice and kill the animals, whereas tumors formed by C2 cells in nude mice do not metastasize and do not kill the host.

Although the compound with structure VII was able to kill the P815 cells, it may exert its effects through a different mechanism. It has been reported that the mutation found in P815 cells alters KIT's substrate specificity (Piao et al, 1996). In this case, the relatively general inhibitor with the structure VII, although not effectively inhibiting phophorylation of the KIT mutant, might still effectively repress other activating effector(s) in the KIT signaling pathway(s), resulting in the death of P815 cells. The fact that a compound which does not inhibit constitutively activated KIT can kill neoplastic mast cells does not detract from the theory that activating c-KIT mutations may be causal events in mastocytosis. Conversely, effective suppression of constitutively activated KIT is directly associated with the ability to kill neoplastic mast cells, supporting this hypothesis.

While the mechanism whereby the compound with the structure VII killed neoplastic P815 cells remains to be elucidated, the present study identifies indolinone-derived tyrosine kinase inhibitors as the first potential therapy aimed at a cause of mastocytosis.

References

Devinney R, Gold W V: Establishment of two dog mastocytoma cell lines in continuous culture. *Am J Respir Cell Mol Biol* 3: 413–420, 1990

Dunn T B, Potter M: A transplantable mast-cell neoplasm in the mouse. *J Natl Cancer Inst* 18: 587–601, 1957

Furitsu T, Tsujimura T, Tono T, Ikeda H, Kitayama H, et al: Identification of mutations in the coding sequence of the proto-oncogene c-kit in a human mast cell leukemia cell line causing ligand-independent activation of c-kit product. *J Clin Invest* 92: 1736–1744, 1993

Hirota S, Isozaki K, Moriyama Y, Hashimoto K, Nishida T, et al: Gain-of-function mutations of c-kit in human gastrointestinal stromal tumors. *Science* 279: 577–580, 1998

Kitayama H, Kanakura Y, Furitsu T, Tsujimura T, Oritani K, et al: Constitutively activating mutations of c-kit receptor tyrosine kinase confer factor-independent growth and tumorigenicity of factor-dependent hematopoietic cell lines. *Blood* 85: 790–798, 1995

Lazarus S C, DeVinney R, McCabe L J, Finkbeiner W E, Elias D J, Gold W M: Isolated canine mastocytoma cells: propagation and characterization of two cell lines. *Am J Physiol* 251: C935–944, 1986

Longley B J, Tyrrell L, Lu S, Ma Y, Langley K, et al: Somatic c-KIT activating mutation in urticaria pigmentosa and aggressive mastocytosis: establishment of clonality in a human mast cell neoplasm. *Nature Genet* 12: 312–314, 1996

Longley B J, Metcalfe D D, Tharp M, Wang X, Tyrrell L, et al: Activating and dominant inactivating c-KIT catalytic domain mutations in distinct clinical forms of human mastocytosis. *Proc Natl Acad Sci USA* 96: 1609–1614, 1999

Ma Y, Longley B J, Wang X, Blount J L, Langley K, Caughey G H: Clustering of activating mutations in c-KIT's juxtamembrane coding region in canine mast cell neoplasms. *J Invest Dermatol* 112: 165–170, 1999a Ma Y, Cunningham M E, Wang X, Ghosh I, Regan L, Longley B J: Inhibition of spontaneous receptor phosphorylation by residues in a putative $\alpha$-helix in the KIT intracellular juxtamembrane region. *J Biol Chem* 274: 13399–13402, 1999b Martin F H, Suggs S V, Langley K E, Lu H S, Ting J, et al: Primary structure and functional expression of rat and human stem cell factor DNAs. *Cell* 63: 203–211, 1990

Mohammadi M, McMahon G, Sun L, Tang C, Hirth P, et al: Structures of the tyrosine kinase domain of fibroblast growth factor receptor in complex with inhibitors. *Science* 276: 955–960, 1997

Nagata H, Worobec A S, Oh C K, Chowdhury B A, Tannenbaum S, et al: Identification of a point mutation in the catalytic domain of the protooncogene c-kit in peripheral blood mononuclear cells of patients who have mastocytosis with an associated hematologic disorder. *Proc Natl Acad Sci USA* 92: 10560–10564, 1995

Piao X, Paulson R, Van Der Geer P, Pawson T, Berstein A: Oncogenic mutation in the Kit receptor tyrosine kinase alters substrate specificity and induces degradation of the protein tyrosine phosphatase SHP-1. *Proc Natl Acad Sci USA* 93: 14665–14669, 1996

Qiu F, Ray P, Brown K, Barker P E, Jhanwar S, et al: Primary structure of c-kit: relationship with the CSF-1/PDGF receptor kinase family-oncogenic activation of v-kit involves deletion of extracellular domain and C terminus. *EMBO J* 7: 1003–1011, 1988

Sun L, Tran N, Tang F, App H, Hirth P, McMahon G, Tang C: Synthesis and biological evaluations of 3-substituted indolin-2-ones: a novel class of tyrosine kinase inhibitors that exhibit selectivity toward particular receptor tyrosine kinases. *J Med Chem* 41: 2588–2603, 1998

Tsujimura T, Furitsu T, Morimoto M, Koji K, Nomura S, et al: Ligand-independent activation of c-kit receptor tyrosine kinase in a murine mastocytoma cell line P-815 generated by a point mutation. *Blood* 83: 2619–2626, 1994

Tsujimura T, Morimoto M, Hashimoto K, Moriyama Y, Kitayama H, et al: Constitutive activation of c-kit in FMA3 murine mastocytoma cells caused by deletion of seven amino acids at the juxtamembrane domain. *Blood* 87: 273–283, 1996

Yarden Y, Kuang W-J, Yang-Feng T, Coussens L, Munemitsu S, et al: Human proto-oncogene c-kit: a new cell surface receptor tyrosine kinase for an unidentified ligand. *EMBO J* 6: 3341–3351, 1987

What is claimed:

1. A method of treating in a subject mastocytosis which comprises administering to the subject a therapeutically effective amount of a compound having the structure:

(Structure I)

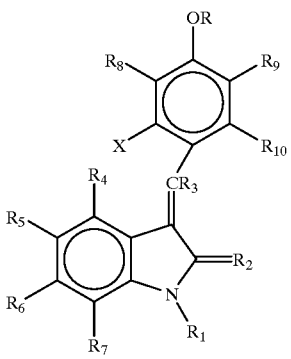

or a pharmaceutically acceptable salt thereof so as to thereby treat mastocytosis in the subject, wherein $R_1$ is H or alkyl; $R_2$ is O or S; $R_3$ is hydrogen;

$R_4$, $R_5$, $R_6$, and $R_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

$R_8$, $R_9$, and $R_{10}$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; x is Br, Cl, F or I; each of R and R' is independently H, alkyl or aryl.

2. A method of treating in a subject mastocytosis which comprises administering to the subject a therapeutically effective amount of a compound having the structure:

(Structure II)

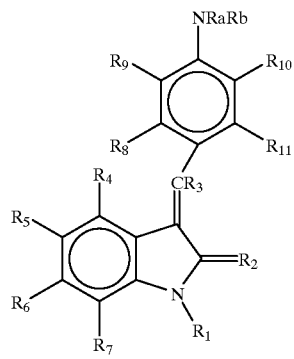

or a pharmaceutically acceptable salt thereof so as to thereby treat mastocytosis in the subject, wherein $R_1$ is H or alkyl; $R_2$ is O or S; $R_3$ is hydrogen;

$R_4$, $R_5$, $R_6$ and $R_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

$R_8$, $R_9$, $R_{10}$ and $R_{11}$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

Ra and Rb are each independently hydrogen, alkyl and C(O)R, or NRaRb taken together may be a heterocyclic ring of 3 to 8 atoms optionally substituted at one or more positions with hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; x is Br, Cl, F or I; and each of R and R' is independently H, alkyl or aryl.

3. A method of treating in a subject mastocytosis which comprises administering to the subject a therapeutically effective amount of a compound having the structure:

(Structure III)

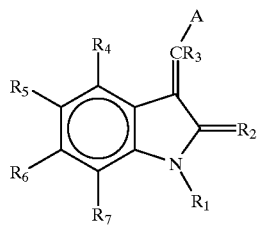

or a pharmaceutically acceptable salt thereof so as to thereby treat mastocytosis in the subject, wherein $R_1$ is H or alkyl; $R_2$ is O or S; $R_3$ is hydrogen;

R$_4$, R$_5$, R$_6$, and R$_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

A is a five membered heteroaryl ring thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, or tetrazole, optionally substituted at one or more positions with alkyl, alkoxy, aryl, aryloxy, alkaryl, alkaryloxy, halogen, trihalomethyl, S(O)R, SO$_2$NRR', SO$_3$R, SR, NO2, NRR', OH, CN, C(O)R, OC(O)R, NHC(O)R, (CH$_2$)$_n$CO2R, or CONRR';

n is 0–3; x is Br, Cl, F or I; and each of R and R' is independently H, alkyl or aryl.

4. A method of treating in a subject mastocytosis which comprises administering to the subject a therapeutically effective amount of a compound having the structure:

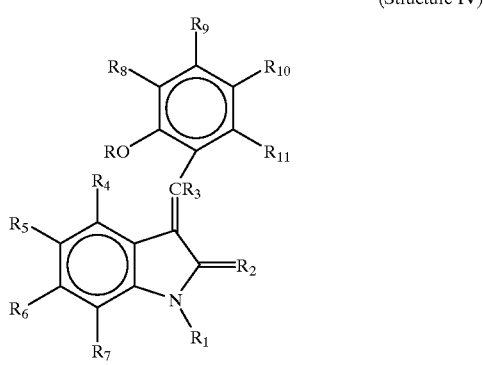

(Structure IV)

or a pharmaceutically acceptable salt thereof so as to thereby treat mastocytosis in the subject, wherein R$_1$ is H or alkyl; R$_2$ is O or S; R$_3$ is hydrogen;

R$_4$, R$_5$, R$_6$, and R$_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

R$_8$, R$_9$ and R$_{10}$ and R$_{11}$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; x is Br, Cl, F or I; each of R and R' is independently H, alkyl or aryl.

5. A method of treating in a subject mastocytosis which comprises administering to the subject a therapeutically effective amount of a compound having the structure:

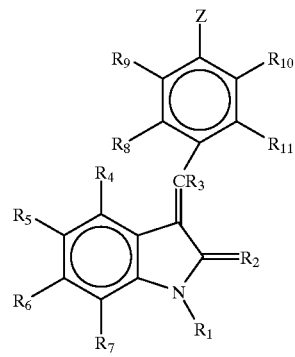

(Structure V)

or a pharmaceutically acceptable salt thereof so as to thereby treat mastocytosis in the subject, wherein R$_1$ is H or alkyl; R$_2$ is O or S; R$_3$ is hydrogen;

R$_4$, R$_5$, R$_6$, and R$_7$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

R$_8$, R$_9$, R$_{10}$ and R$_{11}$ are each independently hydrogen, alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO2R, or CONRR';

n is 0–3; Z is Br, Cl, F, I, methyl, ethyl, n-propyl, iso-propyl, n-butyl, iso-butyl, or tert-butyl; and each of R and R' is independently H, alkyl or aryl.

6. A method of treating in a subject mastocytosis which comprises administering to the subject a therapeutically effective amount of a compound having the structure:

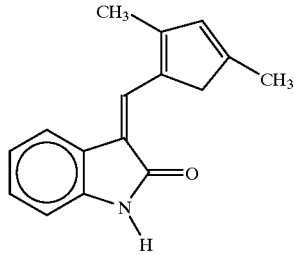

(Structure VI)

or a pharmaceutically acceptable salt thereof so as to thereby treat mastocytosis in the subject.

7. A method of treating in a subject mastocytosis which comprises administering to the subject a therapeutically effective amount of a compound having the structure:

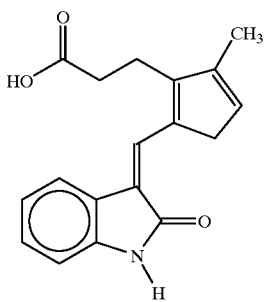

(Structure VIII)

or a pharmaceutically acceptable salt thereof so as to thereby treat mastocytosis in the subject.

8. The method of any one of claims 1–6 and 7, which comprises inhibiting the kinase enzymatic reaction of kit protein.

9. The method of any one of claims 1–6 and 7, wherein downstream signaling of the kit activation pathway is inhibited by blocking substrate association with kit kinase domain.

10. The method of any one of claims 1–6 and 7, wherein downstream signaling of the kit activation pathway is inhibited by blocking enzymatic function in the downstream signaling pathway.

11. The method of any one of claims 1–6 and 7, wherein downstream signaling of the kit activation pathway is inhibited by blocking binding of molecules in the downstream signaling pathway.

12. The method of any one of claims 1–6 and 7, wherein the subject is a mammal.

13. The method of claim 12, wherein the mammal is a human being.

14. The method of claim 9, wherein the compound is a small molecule or peptide.

15. The method of claim 9, wherein the compound has the structure:

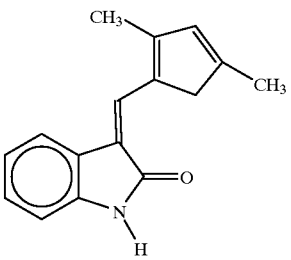

(Structure VI)

or is a pharmacuetically acceptable salt thereof.

16. The method of claim 15, wherein the subject is a canine or a human being.

17. The method of any one of claims 1–6 and 7, wherein the compound is admixed with a carrier.

18. The method of any one of claims 1–6 and 7, wherein the administration is intralesional, intraperitoneal, intramuscular, subcutaneous, intravenous, liposome mediated delivery, transmucosal, intestinal, topical, nasal, oral, anal, ocular or by otic delivery.

19. The method of any one of claims 1–6 and 7, wherein the therapeutically effective amount is from about 1 mg/kg to about 1000 mg/kg.

20. The method of any one of claims 1–6 and 7, wherein the pharmaceutically acceptable salt is a hydrochloride salt, a mesylate salt, an ethylsulfonate salt, or a sulfate salt.

* * * * *